(12) United States Patent
Chen et al.

(10) Patent No.: US 10,561,399 B2
(45) Date of Patent: *Feb. 18, 2020

(54) ULTRASONIC PROBE, CONNECTION COMPONENT FOR ARRAY ELEMENTS AND ULTRASONIC IMAGING SYSTEM THEREOF

(71) Applicant: Shenzhen Mindray Bio-Medical Electronics Co., Ltd., Shenzhen (CN)

(72) Inventors: Zhenyu Chen, Shenzhen (CN); Ming Tang, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/188,583

(22) Filed: Nov. 13, 2018

(65) Prior Publication Data

US 2019/0254628 A1  Aug. 22, 2019

Related U.S. Application Data

(63) Continuation of application No. 14/744,799, filed on Jun. 19, 2015, now Pat. No. 10,123,776, which is a
(Continued)

(51) Int. Cl.
*A61B 8/00* (2006.01)
*B06B 1/06* (2006.01)
(Continued)

(52) U.S. Cl.
CPC ............ *A61B 8/4494* (2013.01); *A61B 8/145* (2013.01); *A61B 8/4444* (2013.01); *A61B 8/56* (2013.01);
(Continued)

(58) Field of Classification Search
CPC ....... A61B 8/44; A61B 8/4444; A61B 8/4494; A61B 8/145; B06B 1/0622; H01L 41/0475; H01L 41/183
See application file for complete search history.

(56) References Cited

U.S. PATENT DOCUMENTS 4,890,268 A * 12/1989 Smith .................. B06B 1/0629
 367/138
5,329,498 A * 7/1994 Greenstein ............ B06B 1/0629
 310/327

(Continued)

FOREIGN PATENT DOCUMENTS

CN 101103927 A 1/2008

*Primary Examiner* — Timothy J Thompson
*Assistant Examiner* — Rhadames Alonzo Miller
(74) *Attorney, Agent, or Firm* — Kory D. Christensen

(57) ABSTRACT

A connection component for array elements in an ultrasonic probe comprises a first-layer body and a second-layer body, wherein the second-layer body is connected with the first-layer body, and an area of the second-layer body is smaller than an area of the first-layer body. A region in the first-layer body that extends beyond the second-layer body is provided with at least one first-layer conductive element penetrating through the first-layer body. A lower surface of the second-layer body is provided with at least one second-layer conductive element penetrating through the second-layer body and the first-layer body. A signal transmission line is connected to the array elements by the first-layer conductive elements and the second-layer conductive elements. The connection component for array elements is in a stepped shape. The signal transmission line is connected to an array element assembly through the stepped connection component for array elements to provide sufficient space.

12 Claims, 10 Drawing Sheets

Related U.S. Application Data continuation of application No. PCT/CN2013/081908, filed on Aug. 20, 2013.

(51) Int. Cl.
  *H01L 41/047* (2006.01)
  *H01L 41/18* (2006.01)
  *A61B 8/14* (2006.01)

(52) U.S. Cl.
  CPC ........ B06B 1/0622 (2013.01); H01L 41/0475 (2013.01); H01L 41/183 (2013.01)

(56) References Cited

U.S. PATENT DOCUMENTS

| | | | | |
|---|---|---|---|---|
| 5,410,205 A * | 4/1995 | Gururaja | B06B 1/0614 | 310/321 |
| 5,559,388 A * | 9/1996 | Lorraine | B06B 1/0622 | 310/327 |
| 5,744,898 A * | 4/1998 | Smith | B06B 1/064 | 310/334 |
| 6,238,481 B1 * | 5/2001 | Yamashita | B06B 1/0622 | 117/84 |
| 6,308,389 B1 * | 10/2001 | Tezuka | B06B 1/0629 | 264/263 |
| 6,625,854 B1 * | 9/2003 | Sudol | B06B 1/0662 | 29/25.35 |
| 6,736,779 B1 * | 5/2004 | Sano | A61B 8/00 | 600/447 |
| 7,288,069 B2 * | 10/2007 | Takeuchi | B06B 1/0622 | 310/335 |
| 7,791,252 B2 * | 9/2010 | Baumgartner | A61B 8/00 | 310/334 |
| 2003/0085635 A1 * | 5/2003 | Davidsen | B06B 1/0607 | 310/334 |
| 2003/0189391 A1 * | 10/2003 | Shimizu | B06B 1/0622 | 310/334 |
| 2007/0145860 A1 * | 6/2007 | Aoki | A61B 8/4281 | 310/334 |
| 2009/0062656 A1 * | 3/2009 | Hyuga | A61B 8/12 | 600/459 |
| 2010/0066207 A1 * | 3/2010 | Saito | A61B 8/4281 | 310/335 |
| 2011/0062824 A1 * | 3/2011 | Wada | B06B 1/0622 | 310/334 |
| 2014/0013850 A1 * | 1/2014 | Kim | G01N 29/2406 | 73/640 |
| 2015/0099960 A1 * | 4/2015 | Ryu | A61B 8/4444 | 600/407 |

\* cited by examiner

ULTRASONIC PROBE, CONNECTION COMPONENT FOR ARRAY ELEMENTS AND ULTRASONIC IMAGING SYSTEM THEREOF

CROSS-REFERENCE

This application is a continuation of Patent Cooperation Treaty Application No. PCT/CN2013/081908, filed Dec. 20, 2012, which is hereby incorporated by reference.

TECHNICAL FIELD

The present disclosure relates to ultrasonic diagnosis, and more particularly to ultrasonic probes.

BRIEF SUMMARY

The present disclosure relates to ultrasonic probes, in particular to ultrasonic probes, and connection components for array elements and ultrasonic imaging systems thereof.

BRIEF DESCRIPTION OF THE DRAWINGS

Objects, features and advantages of the present disclosure will be more obvious by detailed description of preferred embodiments of the present disclosure illustrated in drawings. In the drawings, same reference numerals represent the same parts, with a focus on illustrating the principle of the present disclosure instead of proportionally scaling the drawings deliberately based on actual sizes.

DETAILED DESCRIPTION

Figure 1:
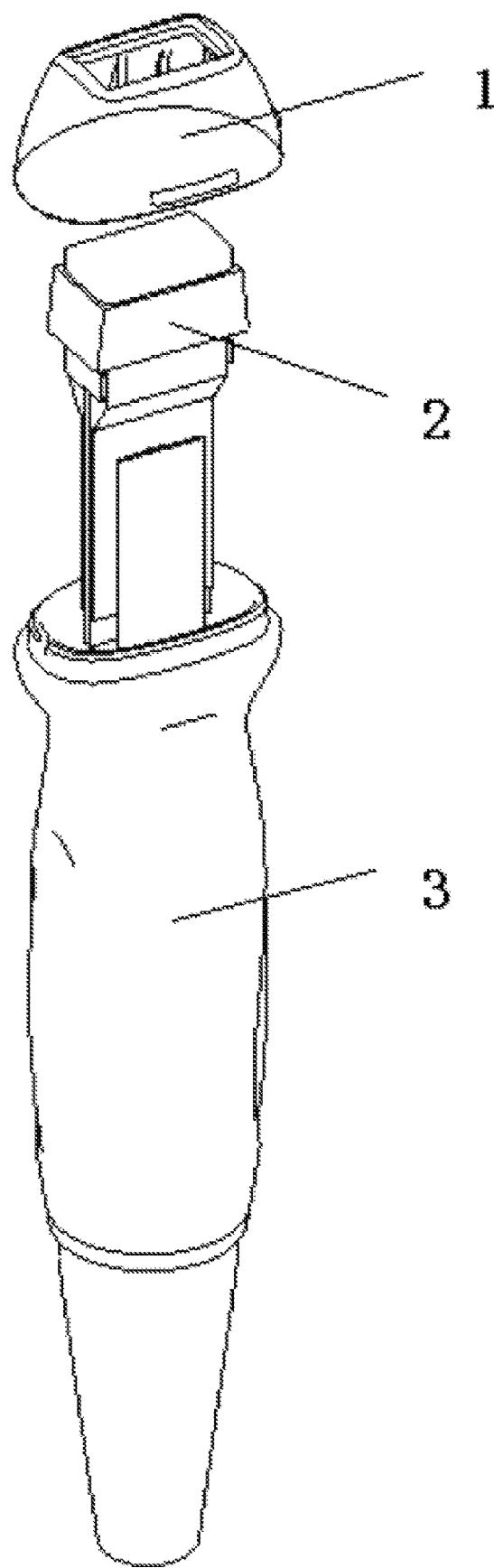
FIG. 1 is an exploded perspective view of an ultrasonic probe in one embodiment.

In a medical ultrasonic imaging system, an ultrasonic probe is used for emitting ultrasonic waves and receiving echoes carrying information on human tissues. A common ultrasonic probe consists generally of an ultrasonic head housing, a transducer, and a handle module, wherein the transducer is a device for emitting ultrasonic waves and receiving echoes. The transducer is a core part of the ultrasonic probe, which consists generally of a matching layer, a wafer, a flexible printed circuit board (FPC) and a backing block. One-dimensional (1-D) ultrasonic probes are widely used at present. With respect to a 1-D ultrasonic probe, array elements of the transducer are usually arranged in a 1-D direction, and an electrical connection of the array elements is drawn from both sides of the FPC.

Two-dimensional (2-D) matrix ultrasonic probes have found an increasingly wide utilization. The difference between 1-D ultrasonic probes and 2-D matrix ultrasonic probes is that array elements of transducer in a 2-D matrix ultrasonic probe are arranged along two dimensions to form an array of transducer array elements, that is, there are a total of M×N transducer array elements, wherein M is the number of rows in the array and N is the number of columns in the array. There are usually thousands of array elements in the transducer of the 2-D matrix ultrasonic probe. Therefore, making an interconnection between the transducer elements and their corresponding controlling elements (such as chips, high-voltage switches, etc.) in the 2-D matrix ultrasonic probe may be a challenge. When the 2-D ultrasonic probe adopts the interconnection manner employed by the transducer of the 1-D ultrasonic probe, the circuits of FPCs or printed circuit boards (PCBs) may be very dense and even intricate due to numerous transducer array elements, which is beyond the manufacturing capacity of FPCs and PCBs. Some existing interconnection methods used to connect the transducer array elements and their corresponding controlling elements in the 2-D matrix ultrasonic probe may have a high registration requirement, a complicated process, and a high cost.

It might be necessary to provide a connection component for array elements which can provide sufficient space for connecting signal transmission lines to array elements, and an ultrasonic probe including the connection component for array elements and an ultrasonic imaging system thereof.

The connection component for array elements in an ultrasonic probe may include a first-layer body, a second-layer body, a first-layer conductive element and a second-layer conductive element. The first-layer body may have a first upper surface and a first lower surface. The second-layer body may have a second upper surface and a second lower surface. The second upper surface may contact with the first lower surface, and an area of the second upper surface may be smaller than an area of the first lower surface. A region in the first lower surface that extends beyond the second upper surface may form a first-layer wiring connection region. The second lower surface may then form a second-layer wiring connection region. The first-layer conductive element may be arranged on the first-layer wiring connection region and may pass through the first body and extend to the first upper surface. The second-layer conductive element may be arranged on the second-layer wiring connection region and may pass through the second-layer body and the first-layer body, and extend to the first upper surface of the first-layer body.

In one embodiment, the connection component for array elements may further include a third-layer body and a third-layer conductive element. The third-layer body may have a third upper surface and a third lower surface. The third upper surface may contact with the second lower surface. An area of the third upper surface may be smaller than an area of the second lower surface. A region in the second lower surface that extends beyond the third upper surface may form a second-layer wiring connection region. The third lower surface may form a third-layer wiring connection region thereon. The third-layer conductive element may be arranged on the third-layer wiring connection region and may pass through the third-layer body, the second-layer body and the first-layer body, and then extend to the first upper surface of the first-layer body.

The ultrasonic probe may include a transducer. The transducer may include an array element assembly, a connection component for array elements, a first-group signal transmission line and a second-group signal transmission line. The array element assembly may have a plurality of array elements. The connection component for array elements may include a first-layer body, a second-layer body, a plurality of first-layer conductive elements and a plurality of second-layer conductive elements. The first-layer body may have a first upper surface and a first lower surface. A plurality of conductive contacts may be arranged on the first upper surface. Each conductive contact may be connected to one of the array elements. The second-layer body may have a second upper surface and a second lower surface. The second upper surface may contact the first lower surface. An area of the second upper surface may be smaller than an area of the first lower surface. A region in the first lower surface that extends beyond the second upper surface may form a first-layer wiring connection region. A second lower surface may form a second-layer wiring connection region. The plurality of first-layer conductive elements may be arranged on the first-layer wiring connection region. The plurality of first-layer conductive elements may pass through the first-layer body and extend to the first upper surface of the first-layer body. Each first-layer conductive element may be connected to one of the conductive contacts. The plurality of second-layer conductive elements may be arranged on the second-layer wiring connection region. The plurality of second-layer conductive elements may pass through the second-layer body and the first-layer body and extend to the first upper surface of the first-layer body. Each second-layer conductive element may be connected to one of the conductive contacts. The first-group signal transmission line may be connected to the plurality of first-layer conductive elements. The second-group signal transmission line may be connected to the plurality of second-layer conductive elements.

In one embodiment, the first-group signal transmission line may include a first-group substrate layer and a first-group wire formed on the first-group substrate layer. The second-group signal transmission line may include a second-group substrate layer and a second-group wire formed on the second-group substrate layer. The second-layer body may be an extension of the first-group substrate layer. The first-group wire may be connected to the first-layer conductive elements. The second-group wire may be connected to the second-layer conductive elements.

In another embodiment, the connection component for array elements may further include a third-layer body and a plurality of third-layer conductive elements. The third-layer body may have a third upper surface and a third lower surface. The third upper surface may contact the second lower surface. An area of the third upper surface may be smaller than an area of the second lower surface. A region in the second lower surface that extends beyond the third upper surface may form a second-layer wiring connection region. The third lower surface may form a third-layer wiring connection region. The plurality of third-layer conductive elements may be arranged on the third-layer wiring connection region. Third-layer conductive elements may pass through the third-layer body, the second-layer body and the first-layer body and extend to the first upper surface of the first-layer body. Each third-layer conductive element may be connected to one of the conductive contacts. The ultrasonic transducer may further include a third-group signal transmission line connected to the plurality of third-layer conductive elements.

In still another embodiment, the first-group signal transmission line may include a first-group substrate layer and a first-group wire formed on the first-group substrate layer. The second-group signal transmission line may include a second-group substrate layer and a second-group wire formed on the second-group substrate layer. The third-group signal transmission line may include a third-group substrate layer and a third-group wire formed on the third-group substrate layer. The second-layer body may be an extension of the first-group substrate layer. The third-layer body may be an extension of the second-group substrate layer. The first-group wire may be connected to the first-layer conductive element. The second-group wire may be connected to the second-layer conductive element. The third-group wire may be connected to the third-layer conductive element.

In another embodiment, the first upper surface may be provided with a plurality of conductive contacts. Each conductive contact is electrically connected to one of the array elements.

In another embodiment, each array element may include a transducer element and a backing block connected to the transducer element.

In another embodiment, the first-layer body, the second-layer body and the backing block may be made of same material.

The ultrasonic imaging system may include any one of the foregoing ultrasonic probes.

In the foregoing embodiments, the connection component for array elements may be in a stepped shape. The signal transmission line may be connected to an array element assembly through the stepped connection component; thus there might be sufficient space for an interconnection between the signal transmission line and the array element assembly.

To make it easier to understand the present disclosure, all technical and scientific terms used herein have the same meaning as commonly understood by those skilled in the art to which the present disclosure belongs. The preferred embodiments of the present disclosure are shown in the drawings. However, the present disclosure can be realized in a variety of forms, without being construed as limited to the described embodiments herein; rather, these embodiments are provided in order to make the present disclosure thorough and complete.

Unless otherwise defined, all technical and scientific terms used herein have the same meaning as commonly understood by those skilled in the art to which the present disclosure belongs. Terms used herein to describe particular embodiments are not intended to limit the present disclosure. As used herein, the term "and/or" includes any and all combinations of one or more of the item being described.

As shown in FIG. 1, the ultrasonic probe in an embodiment may have an ultrasonic head housing 1, a transducer 2 and a handle module 3. The ultrasonic head housing 1 and the handle module 3 may form a receiving cavity when they connect to each other. The transducer 2 may be fixedly accommodated in the receiving cavity. In one embodiment, the position and connection among the ultrasonic head housing 1, the transducer 2 and the handle module 3 may be identical or similar to those in a conventional ultrasonic probe, which will not be described in detail herein.

It may be appreciated that the shape and structure of the probe shown in FIG. 1 are merely illustrated as an exemplary embodiment of the ultrasonic probe of the present disclosure, and are not intended to limit the present disclosure to the probe shown in FIG. 1. For example, the probe in FIG. 1 may be used for heart scans. The disclosures herein can be used in many types of ultrasonic probes. FIG. 1 illustrates just one example of the probe of the present disclosure without a specific description of the exemplary ultrasonic probe, e.g., specifics and details about structure, connection, proportion of components, and so on.

Figure 2:
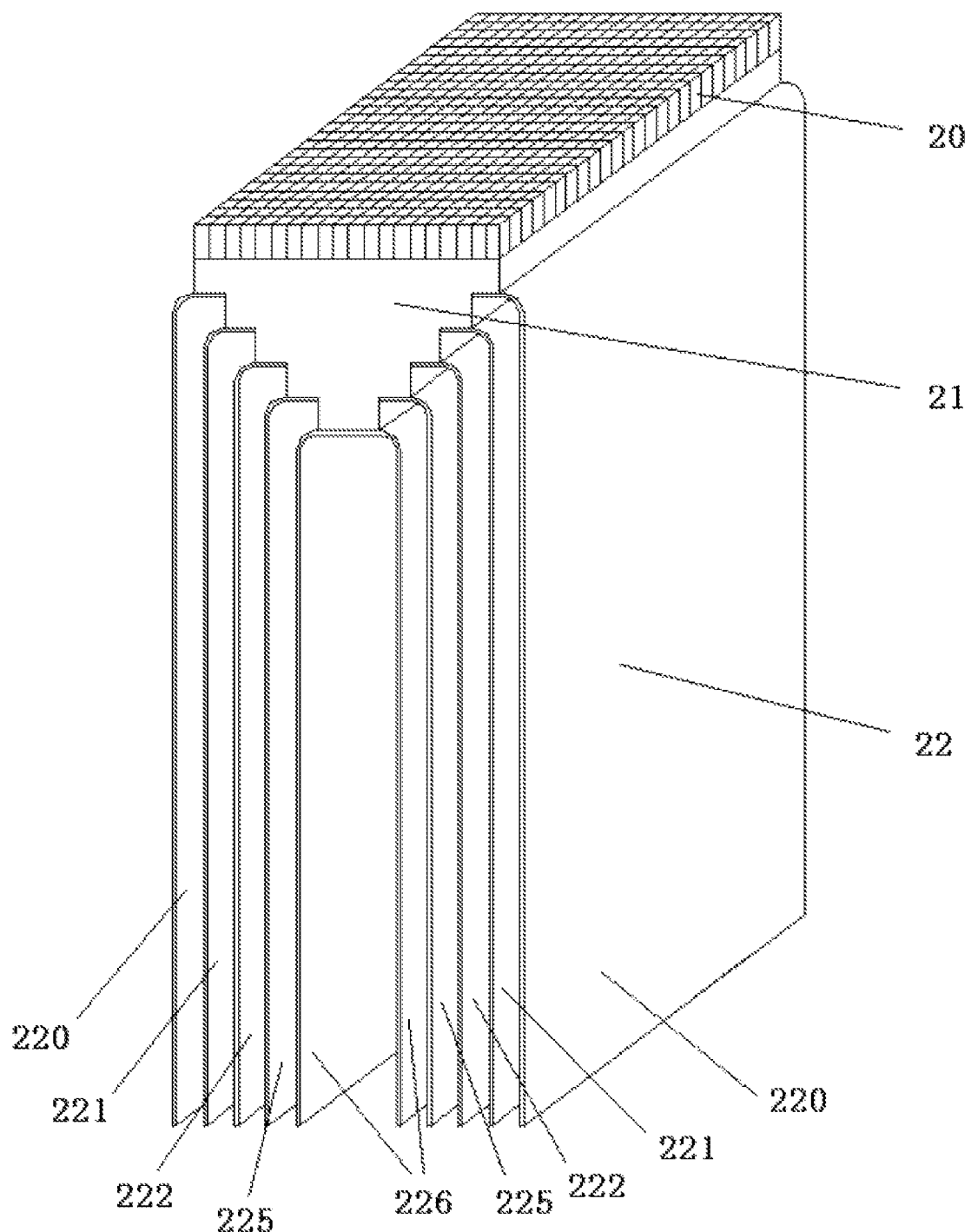
FIG. 2 is a perspective view of a transducer in one embodiment.

In one embodiment in FIG. 2, the transducer 2 may include an array element assembly 20, a connection component for array elements 21 and a signal transmission line component 22.

The array element assembly 20 may include a plurality of array elements. For example, the array element assembly 20 can be an array of M×N array elements, where M is the number of rows and N is the number of columns in the array, and M and N are natural numbers greater than 0. In one embodiment, the arrangement of array elements in the array can be configured freely according to the actual design of the ultrasonic probe, for example, these array elements can be arranged as the aforesaid array of M×N in a rectangular or square shape, where M and N can be any natural numbers greater than 0. Alternatively, they can be arranged in a nearly circular shape, an elliptic shape, or any irregular shape. The quantity of the array elements can be set according to actual requirements and is not limited in the present disclosure.

The array element assembly 20 may be connected to the upper surface of the connection component for array elements 21, and the signal transmission line component 22 can be electrically connected to the array elements in the array element assembly 20 through the connection component for array elements 21 (detailed description below).

Figure 3:
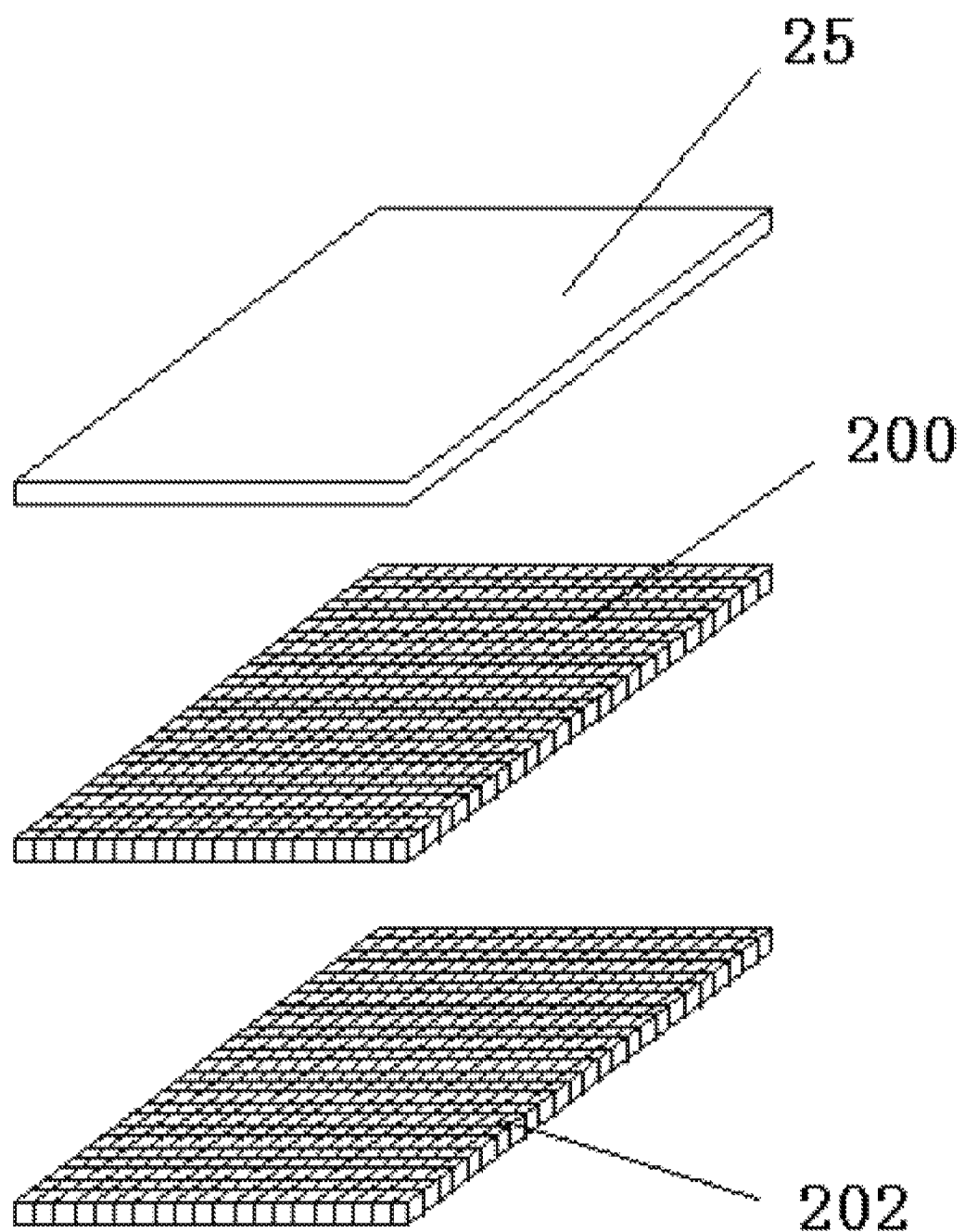
FIG. 3 is an exploded perspective view of an array element assembly in one embodiment.
Figure 4:
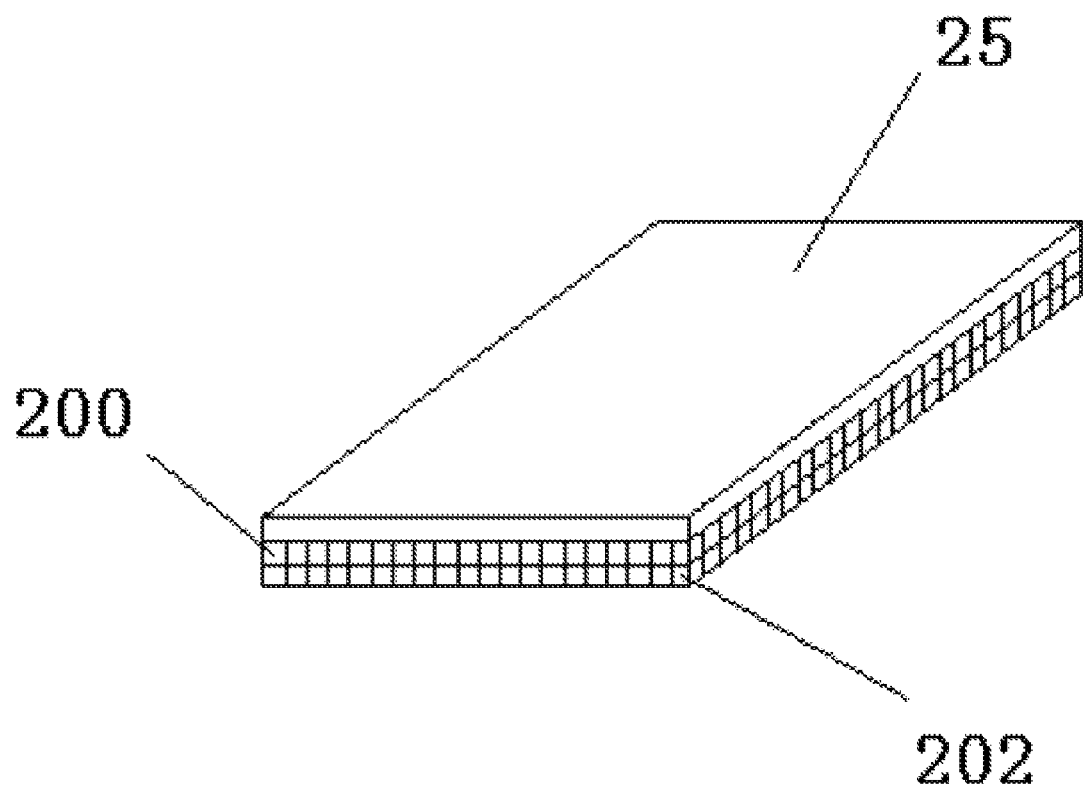
FIG. 4 is a diagram of a combination of the array element assembly in one embodiment.
Figure 5:
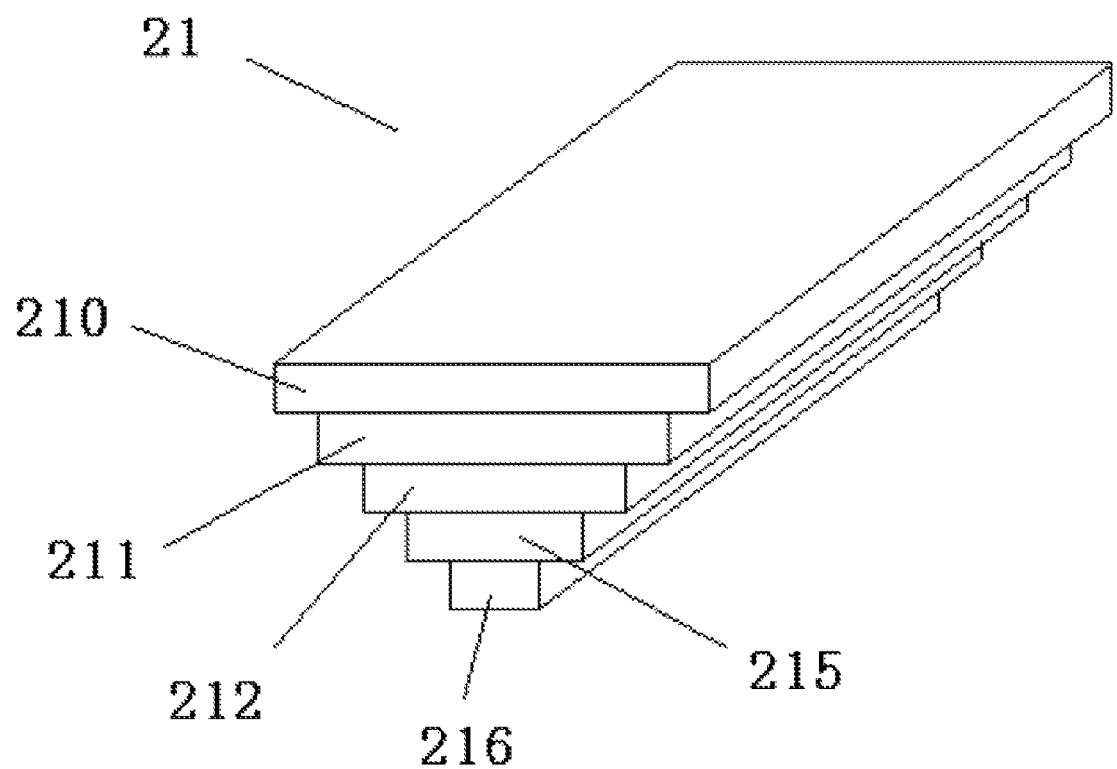
FIG. 5 is a perspective view of a connection component for array elements in one embodiment.
Figure 6:
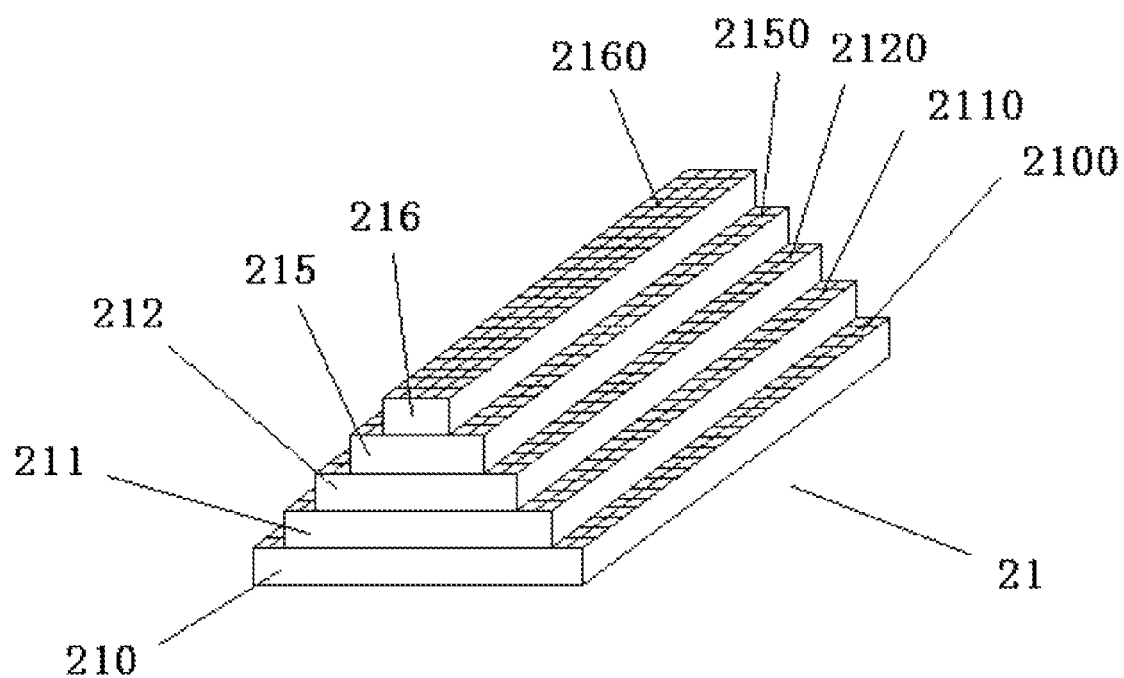
FIG. 6 is another perspective view of the connection component for array elements shown in FIG. 5.

In one embodiment as shown in FIG. 3 and FIG. 4, there may be a matching layer 25 over the array element assembly 20. The matching layer 25 may be any common matching layer currently used in ultrasonic probes, and will not be described in detail herein.

As shown in FIG. 3 and FIG. 4, in one embodiment, each array element in the array element assembly 20 may include a transducer element and a backing block that is below the transducer element. The transducer element and the backing block in each array element may be disposed in a stacked arrangement and electrically connected to each other; that is, the transducer element may be connected to the element connecting component 21 through the backing block in one embodiment.

In another embodiment of the present disclosure, an array element in an array element assembly 20 may be only a transducer element; that is, the transducer element may be directly connected to the connection component for array elements 21 in one embodiment. In this respect, for example, the connection component for array elements 21 and the backing block may be made of similar backing material.

It can be understood that, since an array element assembly 20 is arranged in an array, transducer elements may be arranged to be a transducer element array 200, and backing blocks may be arranged to be a backing block array 202, which is below the transducer element array 200, in one embodiment, where the array element assembly 20 may include the transducer elements and the backing blocks, as shown in FIG. 3 and FIG. 4.

In one embodiment, the connection between transducer elements and backing blocks can be a common conventional connection, which will not be described in detail herein.

As previously described, a connection component for array elements 21 may also be included in one embodiment. FIGS. 5-8 illustrate the connection component for array elements 21 of one embodiment.

In one embodiment, the connection component for array elements 21 can include a plurality of layers of bodies; for example, it can include at least two layers of bodies, three layers of bodies, four layers of bodies, and so forth. For instance, the connection component for array elements 21 shown in FIGS. 5-8 includes five layers of bodies (i.e., 210, 211, 212, 215 and 216). One embodiment shown in FIGS. 5-8 is an example of the connection component for array elements, and the connection component for array elements of the present disclosure is not limited to five bodies. In another embodiment, the number of layers in the bodies may be configured based on an actual design, as long as the connection component for array elements has at least two layers. The examples described below are shown in FIGS. 5-8, but they do not need to be identical.

In one embodiment, the connection component for array elements 21 may include a first-layer body 210, a second-layer body 211, a third-layer body 212, a fourth-layer body 215 and a fifth-layer body 216. Each body may have an upper surface and a lower surface.

Figure 7:
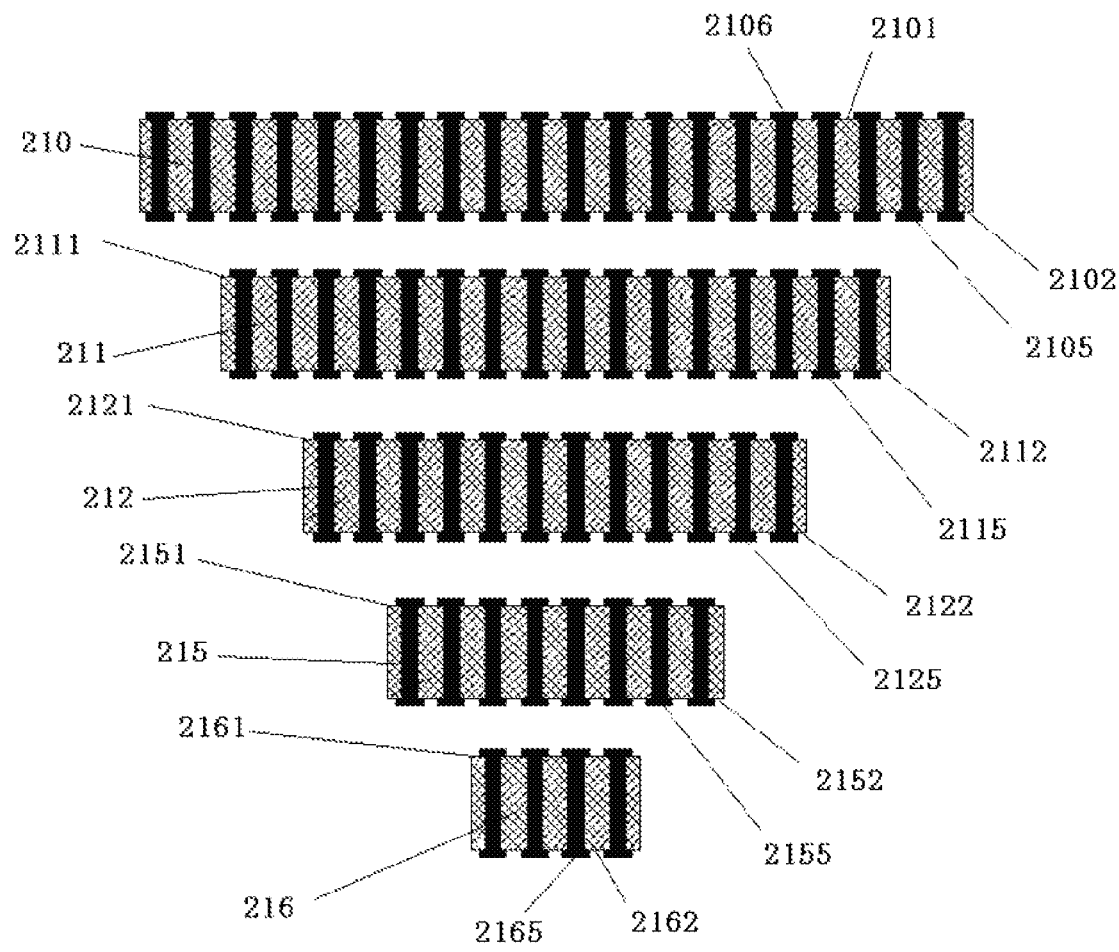
FIG. 7 is a cross-sectional exploded view of a connection component for array elements in one embodiment.

In one embodiment shown in FIG. 7, the first-layer body 210 may have a first upper surface 2101 and a first lower surface 2102; the second-layer body 211 may have a second upper surface 2111 and a second lower surface 2112; the third-layer body 212 may have a third upper surface 2121 and a third lower surface 2122; the fourth-layer body 215 may have a fourth upper surface 2151 and a fourth lower surface 2152; and the fifth-layer body 216 may have a fifth upper surface 2161 and a fifth lower surface 2162.

The second upper surface 2111 of the second-layer body 211 may contact the first lower surface 2102 of the first-layer body 210. An area of the second upper surface 2111 of the second-layer body 211 may be smaller than an area of the first lower surface 2102 of the first-layer body 210, so that at least a region of the first lower surface 2102 of the first-layer body 210 may extend beyond the second upper surface 2111 of the second-layer body 211. The region that extends beyond the second upper surface 2111 in the first lower surface 2102 may form a first-layer wiring connection region 2100 of the first-layer body 210 (see FIG. 6 and FIG. 8).

Similarly, the third upper surface 2121 of the third-layer body 212 may contact the second lower surface 2112 of the second-layer body 211. An area of the third upper surface 2121 of the third-layer body 212 may be smaller than an area of the second lower surface 2112 of the second-layer body 211, so that at least a region of the second lower surface 2112 of the second-layer body 211 may extend beyond the third upper surface 2121 of the third-layer body 212. The region extending out of the third upper surface 2121 in the second lower surface 2112 may form a second-layer wiring connection region 2110 of the second-layer body 211 (see FIG. 6 and FIG. 8).

Similarly, the fourth upper surface 2151 of the fourth-layer body 215 may contact the third lower surface 2122 of the third-layer body 212. An area of the fourth upper surface 2151 of the fourth-layer body 215 may be smaller than an area of the third lower surface 2122 of the third-layer body 212, so that at least a region of the third lower surface 2122 of the third-layer body 212 may extend beyond the fourth upper surface 2151 of the fourth-layer body 215. The region extending out of the fourth upper surface 2151 in the third lower surface 2122 may form a third-layer wiring connection region 2120 of the third-layer body 212 (see FIG. 6 and FIG. 8).

Similarly, the fifth upper surface 2161 of the fifth-layer body 216 may contact the fourth lower surface 2152 of the fourth-layer body 215. An area of the fifth upper surface 2161 of the fifth-layer body 216 may be smaller than an area of the fourth lower surface 2152 of the fourth-layer body 215, so that at least a region of the fourth lower surface 2152 of the fourth-layer body 215 may extend beyond the fifth upper surface 2161 of the fifth-layer body 216. The region extending out of the fifth upper surface 2161 in the fourth lower surface 2152 may form a fourth-layer wiring connection region 2150 of the fourth-layer body 215 (see FIG. 6 and FIG. 8).

In one embodiment, the entire fifth lower surface 2162 of the fifth-layer body 216 may form a fifth-layer wiring connection region 2160 of the fifth-layer body 216; that is, the fifth-layer wiring connection region 2160 of the fifth-layer body 216 is the fifth lower surface 2162. In this respect, the entire lower surface forming the wiring connection region may be referred to as the wiring connection region of the corresponding body.

The first-layer wiring connection region 2100 may be provided with at least a first-layer conductive element 2105 which may pass through the first-layer body 210 and extend to the first upper surface 2101 of the first-layer body 210.

The second-layer wiring connection region 2110 may be provided with at least a second-layer conductive element 2115 which may pass through the second-layer body 211 and the first-layer body 210 and extend to the first upper surface 2101 of the first-layer body 210.

The third-layer wiring connection region 2120 may be provided with at least a third-layer conductive element 2125 which may pass through the third-layer body 212, the second-layer body 211 and the first-layer body 210 and extend to the first upper surface 2101 of the first-layer body 210.

The fourth-layer wiring connection region 2150 may be provided with at least a fourth-layer conductive element 2155 which may pass through the fourth-layer body 215, the third-layer body 212, the second-layer body 211 and the first-layer body 210 and extend to the first upper surface 2101 of the first-layer body 210.

The fifth-layer wiring connection region 2160 (i.e., the fifth lower surface 2162 of the fifth-layer body in one embodiment) may be provided with at least a fifth-layer conductive element 2165 which may pass through the fifth-layer body 216, the fourth-layer body 215, the third-layer body 212, the second-layer body 211 and the first-layer body 210 and extend to the first upper surface 2101 of the first-layer body 210.

In one embodiment, the first upper surface 2101 of the first-layer body 210 can be provided with a plurality of conductive contacts 2106 for electrically connecting to the array element assembly 20. Each conductive contact 2106 may electrically connect to one of the array elements in the array element assembly 20; that is, it may be directly and electrically connected to one of the transducer elements, or it may be indirectly and electrically connected to one of the transducer elements through the backing block of the array element (detailed description below).

It can be appreciated that, in one embodiment, these conductive contacts 2106 may be disposed in the first upper surface 2101 of the first-layer body 210, and may correspond to the array element assembly 20 which is connected to the connection component for array elements 21. For example, each conductive contact 2106 may correspond and electrically connect to one array element of the array element assembly 20. In this respect, position, dimension, spacing and arrangement of the conductive contacts 2106 on the first upper surface 2101 of the first-layer body 210 may correspond to that of the array elements of the array element assembly 20 according to actual requirements.

In one embodiment, the conductive contacts can be realized in any forms and/or materials as long as they can be electrically connected to the array element of the array element assembly 20. For example, in an embodiment, the conductive contacts may be in the form of pads, but they can be in any other suitable form in other embodiments.

As previously described, the first-layer conductive element 2105 on the first-layer wiring connection region 2100 may pass through the first-layer body 210 and extend to the first upper surface 2101 of the first-layer body 210. The first-layer conductive elements 2105 can, for example, pass through the first-layer body 210 via holes formed at the first-layer body 210, extend to the first upper surface 2101 of the first-layer body 210, and electrically connect to the aforementioned plurality of conductive contacts 2106. Each first-layer conductive element 2105 may be connected to one of the conductive contacts 2106.

Similarly, the second-layer conductive elements 2115 on the second-layer wiring connection region 2110 can also, for example, pass through the second-layer body 211 and the first-layer body 210 via holes formed in the second-layer body 211 and the first-layer body 210. They then extend to the first upper surface 2101 of the first-layer body 210, and electrically connect to the aforementioned plurality of conductive contacts 2106. Each second-layer conductive element 2115 may be connected to one of the conductive contacts 2106.

Similarly, the third-layer conductive elements 2125 on the third-layer wiring connection region 2120 can also, for example, pass through the third-layer body 212, the second-layer body 211 and the first-layer body 210 via holes formed in the third-layer body 212, the second-layer body 211 and the first-layer body 210. They then extend to the first upper surface 2101 of the first-layer body 210, and electrically connect to the aforementioned plurality of conductive contacts 2106. Each third-layer conductive element 2125 may be connected to one of the conductive contacts 2106.

Similarly, the fourth-layer conductive elements 2155 on the fourth-layer wiring connection region 2150 can also, for example, pass through the fourth-layer body 215, the third-layer body 212, the second-layer body 211 and the first-layer body 210 via holes formed in the fourth-layer body 215, the third-layer body 212, the second-layer body 211 and the first-layer body 210. They then extend to the first upper surface 2101 of the first-layer body 210, and electrically connect to the aforementioned plurality of conductive contacts 2106. Each fourth-layer conductive element 2155 may be connected to one of the conductive contacts 2106.

Similarly, the fifth-layer conductive element 2165 on the fifth-layer wiring connection region 2160 can also, for example, pass through the fifth-layer body 216, the fourth-layer body 215, the third-layer body 212, the second-layer body 211 and the first-layer body 210 via holes formed in the fifth-layer body 216, the fourth-layer body 215, the third-layer body 212, the second-layer body 211 and the first-layer body 210. They then extend to the first upper surface 2101 of the first-layer body 210, and electrically connect to the aforementioned plurality of conductive contacts 2106. Each fifth-layer conductive element 2165 may be connected to one of the conductive contacts 2106.

In one embodiment, the connection component for array elements may include five layers of bodies; for example, the total amount of the first-layer conductive elements 2105, the second-layer conductive elements 2115, the third-layer conductive elements 2125, the fourth-layer conductive elements 2155 and the fifth-layer conductive elements 2165 may equal the amount of conductive contacts 2106 on the first upper surface 2101 of the first-layer body 210. That is, the first-layer conductive elements 2105, the second-layer conductive elements 2115, the third-layer conductive elements 2125, the fourth-layer conductive elements 2155 and the fifth-layer conductive elements 2165 may correspond one-to-one to conductive contacts 2106 on the first upper surface 2101 of the first-layer body 210.

In one embodiment, each conductive contact 2106 may be part of the conductive element connected thereto, for example, the first-layer conductive elements 2105, the second-layer conductive elements 2115, the third-layer conductive elements 2125, the fourth-layer conductive elements 2155 or the fifth-layer conductive elements 2165, and so forth. That is, the conductive contact may be molded integrally with the conductive element connected thereto.

In one embodiment, conductive elements in each layer of a body, such as the first-layer conductive elements 2105, and the second-layer conductive elements 2115, the third-layer conductive elements 2125, the fourth-layer conductive elements 2155 or the fifth-layer conductive elements 2165 and so forth, can be made of any suitable conductive material, such as copper, silver, gold, or other metal or non-metal conductive material.

Figure 8:
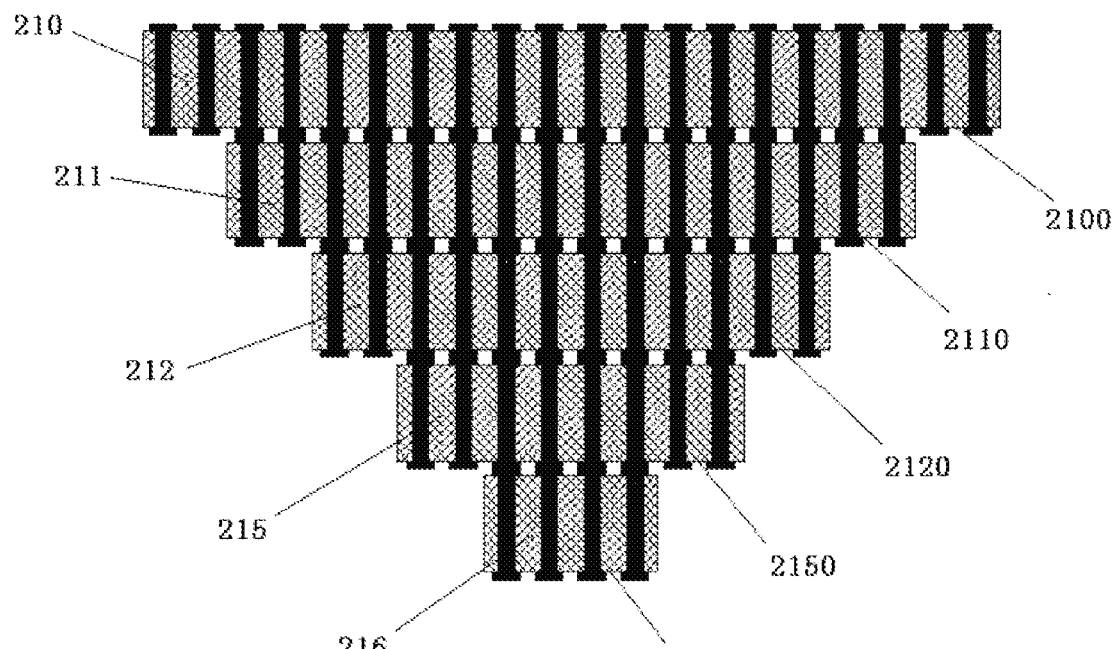
FIG. 8 is a cross-sectional view of a combination of a connection component for array elements shown in FIG. 7.
Figure 9:
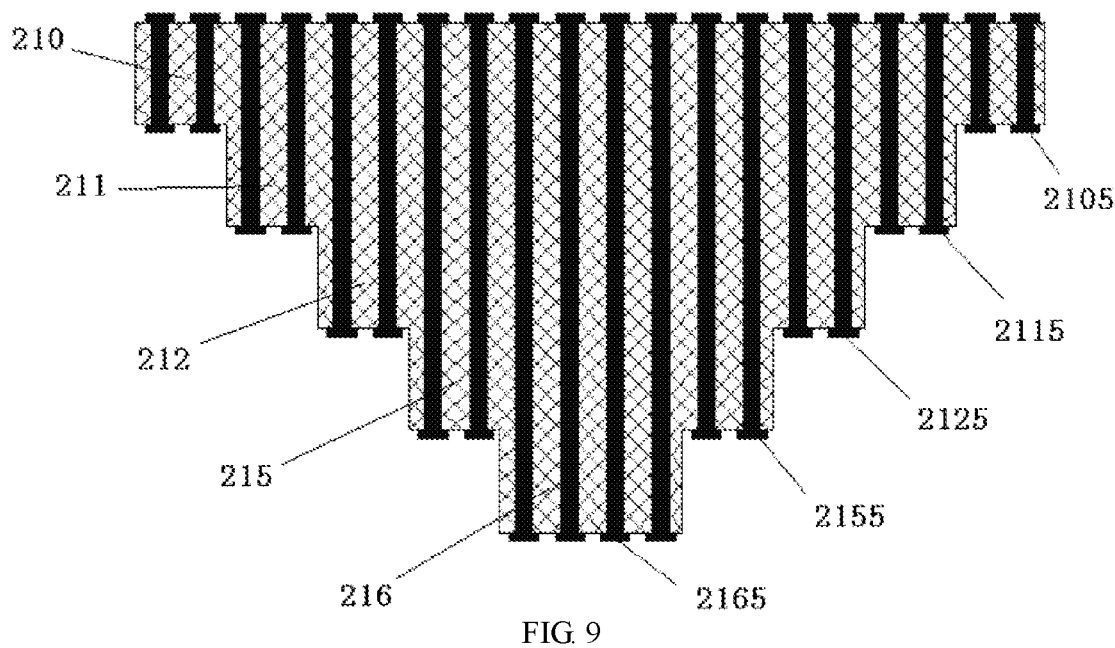
FIG. 9 is a cross-sectional view of a connection component for array elements in another embodiment.

In one embodiment, the fifth-layer body 216, the fourth-layer body 215, the third-layer body 212, the second-layer body 211 and the first-layer body 210 may be separate components and may connect together as shown in FIG. 7 and FIG. 8. In other embodiments of the present disclosure, the fifth-layer body 216, the fourth-layer body 215, the third-layer body 212, the second-layer body 211 and the first-layer body 210 may also be molded integrally as shown in FIG. 9. Herein, one layer of a body combining with another layer of a body also includes these two layers of bodies being molded integrally.

In one embodiment, signal transmission components 22 may include a plurality of groups of signal transmission lines. For example, in one embodiment shown in FIG. 2, signal transmission components 22 may include a first-group signal transmission line 220, a second-group signal transmission line 221, a third-group signal transmission line 222, a fourth-group signal transmission line 225 and a fifth-group signal transmission line 226.

In one embodiment, the first-group signal transmission line 220 may be connected to the first-layer conductive element 2105 which are provided in the first-layer wiring connection region 2100 of the element connecting component 21; the second-group signal transmission line 221 may be connected to the second-layer conductive element 2115 which are provided in the second-layer wiring connection region 2110 of the element connecting component 21; the third-group signal transmission line 222 may be connected to the third-layer conductive element 2125 which are provided in the third-layer wiring connection region 2120 of the element connecting component 21; the fourth-group signal transmission line 225 may be connected to the fourth-layer conductive element 2155 which are provided in the fourth-layer wiring connection region 2150 of the element connecting component 21; and the fifth-group signal transmission line 226 may be connected to the fifth-layer conductive element 2165 which are provided on the fifth-layer wiring connection region 2160 of the element connecting component 21. As previously described, conductive elements in each wiring connection region of the connection component for array elements 21 may be respectively connected to each conductive contact 2106 which are on the first upper surface 2101 of the connection component for array elements 21, and the conductive contacts 2106 may also be respectively connected to each array element in the array element assembly 20. The electrical connection between each group of signal transmission line and each array element of the array element assembly 20 can be achieved by the connection component for array elements 21 in this manner. The ends of these signal transmission lines may be connected to corresponding array element controlling components (not shown in the figures); thus array element assembly 20 will connect to a corresponding array element controlling component to cause a signal transmission.

In one embodiment, each group of signal transmission lines used herein may comprise any suitable types of components for signal transmission of an array element of the array element assembly 20. For example, in one embodiment, each group of signal transmission lines may be a flexible printed circuit board (FPC), or other suitable signal transmission components such as a printed circuit board (PCB), a suitable cable or the like.

In one embodiment, each group of signal transmission lines and each corresponding layer of conductive elements may be connected in any suitable manner, such as by welding and so on.

In one embodiment, each layer of "wiring connection region" (e.g., the first-layer wiring connection region 2100, the second-layer wiring connection region 2110, the third-layer wiring connection region 2120 the fourth-layer wiring connection region 2150 and the fifth-layer wiring connection region 2160) at each layer of the body (e.g., the fifth-layer body 216, the fourth-layer body 215, the third-layer body 212, the second-layer body 211 and the first-layer body 210) may refer to a region where a conductive element is located for connecting with a corresponding signal transmission line, or to a region for connecting with a corresponding signal transmission line.

Figure 10:
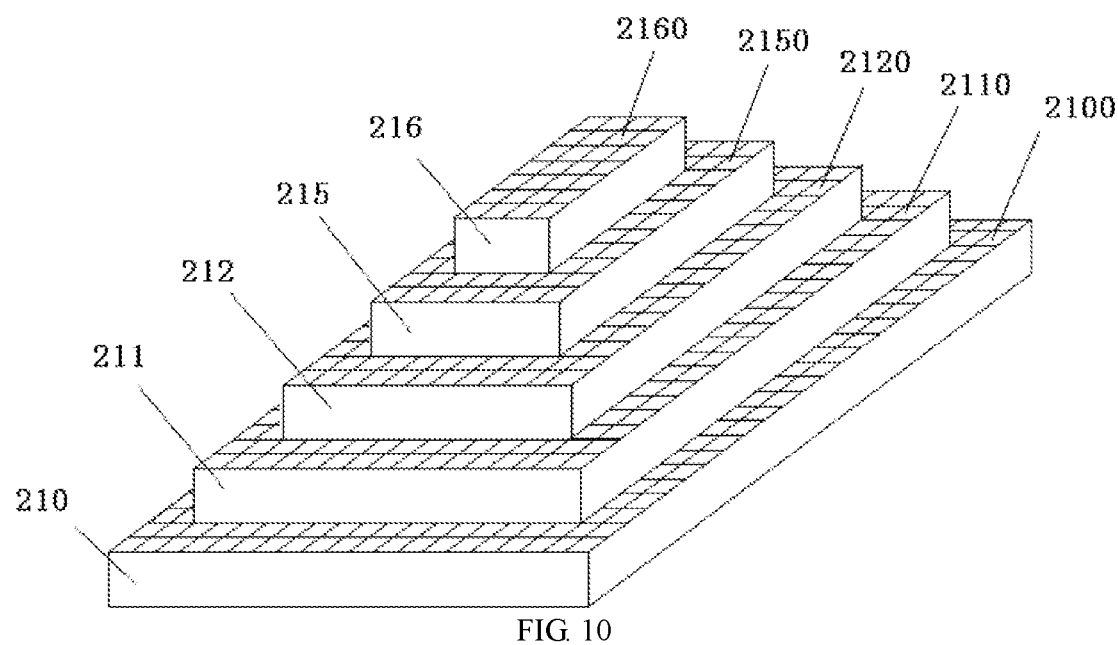
FIG. 10 is a perspective view of a connection component for array elements in another embodiment.

As explained above, each layer of a wiring connection region may be part of the lower surface of each body of the connection component for array elements 21 uncovered by another body, or may be the total lower surface of the body located at the lowest layer. In one embodiment, the wiring connection regions which are formed by part of the lower surface of the body uncovered by another body may have a random shape and/or quantity and may be configured freely and flexibly according to an actual design. For example, in one embodiment as shown in FIG. 10, wiring connection regions of the bodies except the lowest body 216 in the connection component for array elements 21 may be ring-shaped or one embodiment may be bilaterally and/or fore-and-aft symmetrical. It would be understood that the connection component for array elements 21 may be asymmetric, and the whole shape thereof may be configured flexibly based on an actual design.

It would be understood that the wiring connection region of the lowest layer of a body may also be formed by part of the lower surface of the lowest layer of the body instead of the whole lower surface of the lowest layer of the body.

The aforesaid situations herein are uniformly referred to as "forming a wiring connection region" on the lower surface of a corresponding body.

In the foregoing embodiments, the connection component for array elements 21 of the transducer 2 may have five layers of bodies. However, it may have any quantity of layers, which may be flexibly configured according to an actual design and/or the quantity and/or dimensions of the probe, the array element assembly 20, the connection component for array elements and the signal transmission line, as long as it has at least two layers of bodies.

It would be understood that the lower surface of the lowest layer of the body may not be provided with the wiring connection region; instead, the lowest layer of the body may only be used for covering the body adjacent thereto, and the wiring connection region is provided on all or part of the bodies except on the lowest layer.

For example, in another embodiment, the ultrasonic probe may include an ultrasonic head housing 1, a transducer 2 and a handle module 3. The ultrasonic head housing 1 and the handle module 3 may form a receiving cavity when they connect to each other. The transducer 2 may be fixedly accommodated in the receiving cavity. The transducer 2 may include an array element assembly 20, a connection component for array elements 21 and a signal transmission line component 22. It is different from foregoing embodiments in that the connection component for array elements 21 in this embodiment may only have two layers of bodies.

For example, in one embodiment (referring to FIGS. 2-10), the connection component for array elements 21 may have a first-layer body 210 and a second-layer body 211. The first-layer body 210 may have a first upper surface 2101 and a first lower surface 2102; and the second-layer body 211 may have a second upper surface 2111 and a second lower surface 2112.

The second upper surface 2111 of the second-layer body 211 may contact the first lower surface 2102 of the first-layer body 210, and an area of the second upper surface 2111 of the second-layer body 211 may be smaller than an area of the lower surface 2102 of the first-layer body 210. So at least a part of the lower surface 2102 of the first-layer body 210 may extend beyond the second upper surface 2111 of the second-layer body 211, and this region may form a first-layer wiring connection region 2100 of the first-layer body 210.

In one embodiment, the second lower surface 2112 of the second-layer body 211 may provide a second-layer wiring connection region 2110 of the second-layer body.

The first-layer wiring connection region 2100 may be provided with at least a first-layer conductive element 2105 which may pass through the first-layer body 210 and extend to the first upper surface 2101 of the first-layer body 210.

The second-layer wiring connection region 2110 may be provided with at least a second-layer conductive element 2115 which may pass through the second-layer body 211 and the first-layer body 210 and extend to the first upper surface 2101 of the first-layer body 210.

The first upper surface 2101 of the first-layer body 210 may be provided with a plurality of conductive contacts 2106 for electrically connecting to the array element assembly 20. Each conductive contact 2106 may be electrically connected to one of the array elements in the array element assembly 20. The configuration of the conductive contacts can be identical or similar to those in the foregoing embodiments, which will not be repeated herein.

As previously described, the first-layer conductive element 2105 on the first-layer wiring connection region 2100 may pass through the first-layer body 210 and extend to the first upper surface 2101 of the first-layer body 210. For example, the first-layer conductive elements 2105 may pass through the first-layer body 210 via holes formed in the first-layer body 210, extend to the first upper surface 2101 of the first-layer body 210, and electrically connect to the aforementioned plurality of conductive contacts 2106. Each first-layer conductive element 2105 may be connected to one of the conductive contacts 2106.

Similarly, the second-layer conductive elements 2115 on the second-layer wiring connection region 2110 may also pass through the second-layer body 211 and the first-layer body 210 via holes formed in the second-layer body 211 and the first-layer body 210, extend to the first upper surface 2101 of the first-layer body 210, and electrically connect the aforementioned plurality of conductive contacts 2106. Each second-layer conductive element 2115 may be connected to one of the conductive contacts 2106.

In one embodiment, the connection component for array elements may include two layers of bodies; for example, the sum of the first-layer conductive elements 2105 and the second-layer conductive elements 2115 may be equal to the amount of conductive contacts 2106 on the first upper surface 2101 of the first-layer body 210. That is, the first-layer conductive elements 2105 and the second-layer conductive elements 2115 may correspond one-to-one to conductive contacts 2106 on the first upper surface 2101 of the first-layer body 210.

In one embodiment, the second-layer body 211 and the first-layer body 210 which may be separate components which can be connected together, or the second-layer body 211 and the first-layer body 210 may be molded integrally.

In one embodiment, the signal transmission line component 22 may include a first-group signal transmission line 220 and a second-group signal transmission line 221.

In one embodiment, the first-group signal transmission line 220 may be connected to the first-layer conductive element 2105 which is provided on the first-layer wiring connection region 2100 of the element connecting component 21; and the second-group signal transmission line 221 may be connected to the second-layer conductive element 2115 which is provided on the second-layer wiring connection region 2110 of the element connecting component 21. As previously described, conductive elements in each wiring connection region of the connection component for array elements 21 may be respectively connected to each conductive contact 2106 which is in the first upper surface 2101 of the connection component for array elements 21, and the conductive contacts 2106 may also be respectively connected to each array element in the array element assembly 20. Thus, the electrical connection between each group of signal transmission lines and each array element of the array element assembly 20 can be achieved by a connection component for array elements 21 in this manner for signal transmission.

Other features in one embodiment can be identical or similar to those in the foregoing embodiments, which will not be repeated herein.

In still another embodiment, the ultrasonic probe may have an ultrasonic head housing 1, a transducer 2 and a handle module 3. The ultrasonic head housing 1 and the handle module 3 may form a receiving cavity when they connect to each other. The transducer 2 may be fixedly accommodated in the receiving cavity. The transducer 2 may include an array element assembly 20, a connection component for array elements 21 and a signal transmission line component 22. It is different from foregoing embodiments in that the connection component for array elements 21 in this embodiment may only have three layers of bodies.

For example, in one embodiment (still referring to FIGS. 2-10), the connection component for array elements 21 has a first-layer body 210, a second-layer body 211 and a third-layer body 212. The first-layer body 210 may have a first upper surface 2101 and a first-layer lower surface 2102; the second-layer body 211 may have a second upper surface 2111 and a second lower surface 2112; and the third-layer body 212 may include a third upper surface 2121 and a third lower surface 2122.

The second upper surface 2111 of the second-layer body 211 may contact the lower surface 2102 of the first-layer body 210, and an area of the second upper surface 2111 of the second-layer body 211 may be smaller than an area of the lower surface 2102 of the first-layer body 210. So at least a part of the lower surface 2102 of the first-layer body 210 may extend beyond the second upper surface 2111 of the second-layer body 211, and this region may form a first-layer wiring connection region 2100 of the first-layer body 210.

Similarly, the third upper surface 2121 of the third-layer body 212 may contact the third lower surface 2122 of the second-layer body 211, and an area of the third upper surface 2121 of the third-layer body 212 may be smaller than an area of the third lower surface 2122 of the second-layer body 211, so that at least one region of the third lower surface 2122 of the second-layer body 211 may extend beyond the third upper surface 2121 of the third-layer body 212. The region extending out of the third upper surface 2121 in the second lower surface 2112 may form a second-layer wiring connection region 2110 of the second-layer body 211.

In one embodiment, the third lower surface 2122 of the third-layer body 212 may provide a third-layer wiring connection region 2120 of the third-layer body.

The first-layer wiring connection region 2100 may be provided with at least a first-layer conductive element 2105 which may pass through the first-layer body 210 and extend to the first upper surface 2101 of the first-layer body 210.

The second-layer wiring connection region 2110 may be provided with at least a second-layer conductive element 2115 which may pass through the second-layer body 211 and the first-layer body 210 and extend to the first upper surface 2101 of the first-layer body 210.

The third-layer wiring connection region 2120 may be provided with at least a third-layer conductive element 2125 which may pass through the third-layer body 212, the second-layer body 211 and the first-layer body 210 and extend to the first upper surface 2101 of the first-layer body 210.

The first upper surface 2101 of the first-layer body 210 may be provided with a plurality of conductive contacts 2106 for electrically connecting to the array element assembly 20. Each conductive contact 2106 may be electrically connected to one of the array elements in the array element assembly 20. The configuration of the conductive contacts can be identical or similar to those in the foregoing embodiments, which will not be repeated herein.

As previously described, the first-layer conductive element 2105 on the first-layer wiring connection region 2100 may pass through the first-layer body 210 and extend to the first upper surface 2101 of the first-layer body 210. For example, the first-layer conductive element 2105 may pass through the first-layer body 210 via holes formed in the first-layer body 210, extend to the first upper surface 2101 of the first-layer body 210, and electrically connect the aforementioned plurality of conductive contacts 2106. Each first-layer conductive element 2105 may be connected to one of the conductive contacts 2106.

Similarly, the second-layer conductive element 2115 on the second-layer wiring connection region 2110 may also pass through the second-layer body 211 and the first-layer body 210 via holes formed in the second-layer body 211 and the first-layer body 210, extend to the first upper surface 2101 of the first-layer body 210, and electrically connect the aforementioned plurality of conductive contacts 2106. Each second-layer conductive element 2115 may be connected to one of the conductive contacts 2106.

Similarly, the third-layer conductive element 2125 on the third-layer wiring connection region 2120 may also run through the third-layer body 212, the second-layer body 211 and the first-layer body 210 via holes formed at the third-layer body 212, the second-layer body 211 and the first-layer body 210, extend to the first upper surface 2101 of the first-layer body 210, and electrically connect the aforementioned plurality of conductive contacts 2106. Each second-layer conductive element 2125 may be connected to one of the conductive contacts 2106.

In one embodiment, the connection component for array elements may include three layers of bodies; for example, the sum of the first-layer conductive elements 2105, the second-layer conductive elements 2115 and the third-layer conductive elements 2125 may equal the amount of conductive contacts 2106 on the first upper surface 2101 of the first-layer body 210. That is, the first-layer conductive elements 2105, the second-layer conductive elements 2115 and the third-layer conductive elements 2125 may correspond one-to-one to conductive contacts 2106 on the first upper surface 2101 of the first-layer body 210.

In one embodiment, the third-layer body 212, the second-layer body 211 and the first-layer body 210 may be separate components that can be connected together, or the third-layer body 212, the second-layer body 211 and the first-layer body 210 may be molded integrally.

In one embodiment, the signal transmission line component 22 may include a first-group signal transmission line 220, a second-group signal transmission line 221 and a third-group signal transmission line 222.

In one embodiment, the first-group signal transmission line 220 may be connected to the first-layer conductive elements 2105 which are provided in the first-layer wiring connection region 2100 of the element connecting component 21; the second-group signal transmission line 221 may be connected to the second-layer conductive element 2115 which is provided in the second-layer wiring connection region 2110 of the element connecting component 21, and the third-group signal transmission line 222 may connect to the third-layer conductive element 2125 which is provided on the third-layer wiring connection region 2120 of the element connecting component 21. As previously described, conductive elements in each wiring connection region of the connection component for array elements 21 may be respectively connected to each conductive contact 2106 that is in the first upper surface 2101 of the connection component for array elements 21. The conductive contacts 2106 may also be respectively connected to each array element in the array element assembly 20. Thus, the electrical connection between each group of signal transmission lines and each array element of the array element assembly 20 can be achieved by connection component for array elements 21 in this manner for signal transmission.

Other features in one embodiment can be identical or similar to those in foregoing embodiments, which will not be repeated herein.

It would be appreciated that the connection component for array elements 21 may have more layers of bodies.

In some embodiments of the present disclosure, each layer of the body of the connection component for array elements 21 may be made of any suitable material, such as plastic material. In other embodiments of the present disclosure, each layer of the body of the connection component for array elements 21 may be made of backing material for an ultrasonic probe.

In some embodiments, each layer of the body of the connection component for array elements 21 may be made of the same material. In other embodiments, at least one layer of the bodies of the connection component for array elements 21 may be made of material different from that in other layers of the bodies.

Figure 11:
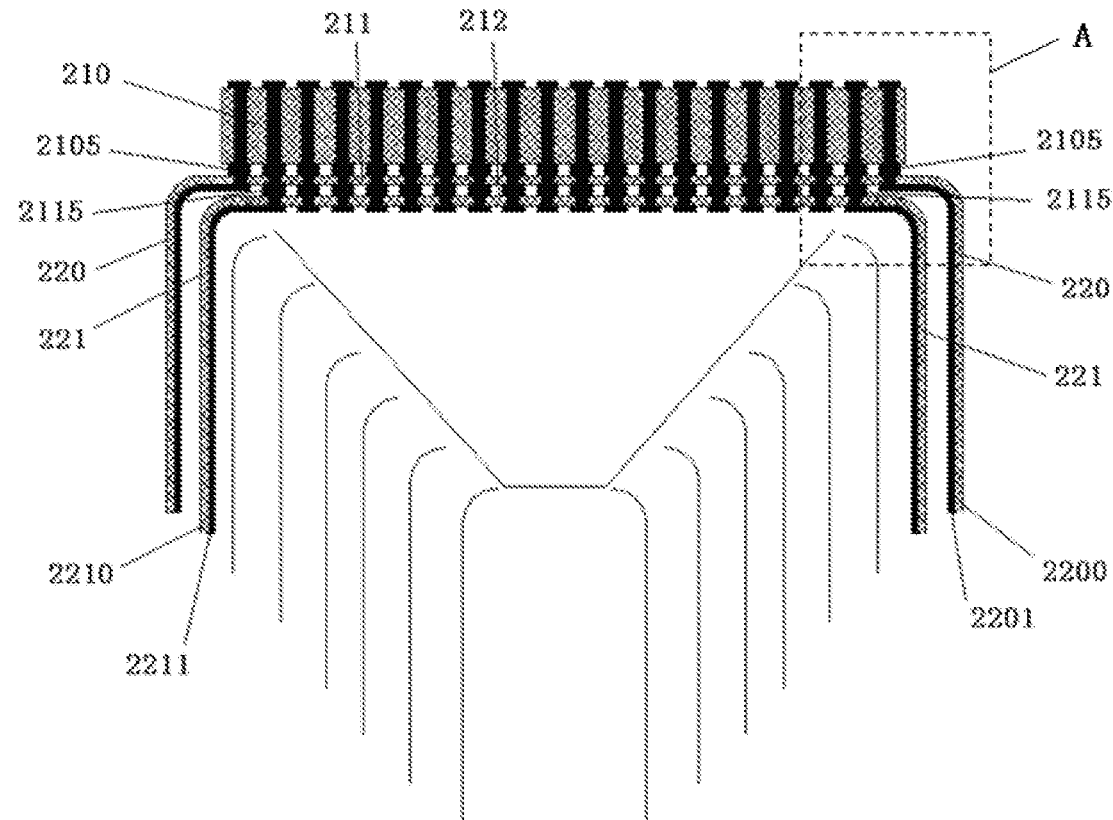
FIG. 11 is a cross-sectional view of a connection component for array elements and a signal transmission component in another embodiment.
Figure 12:
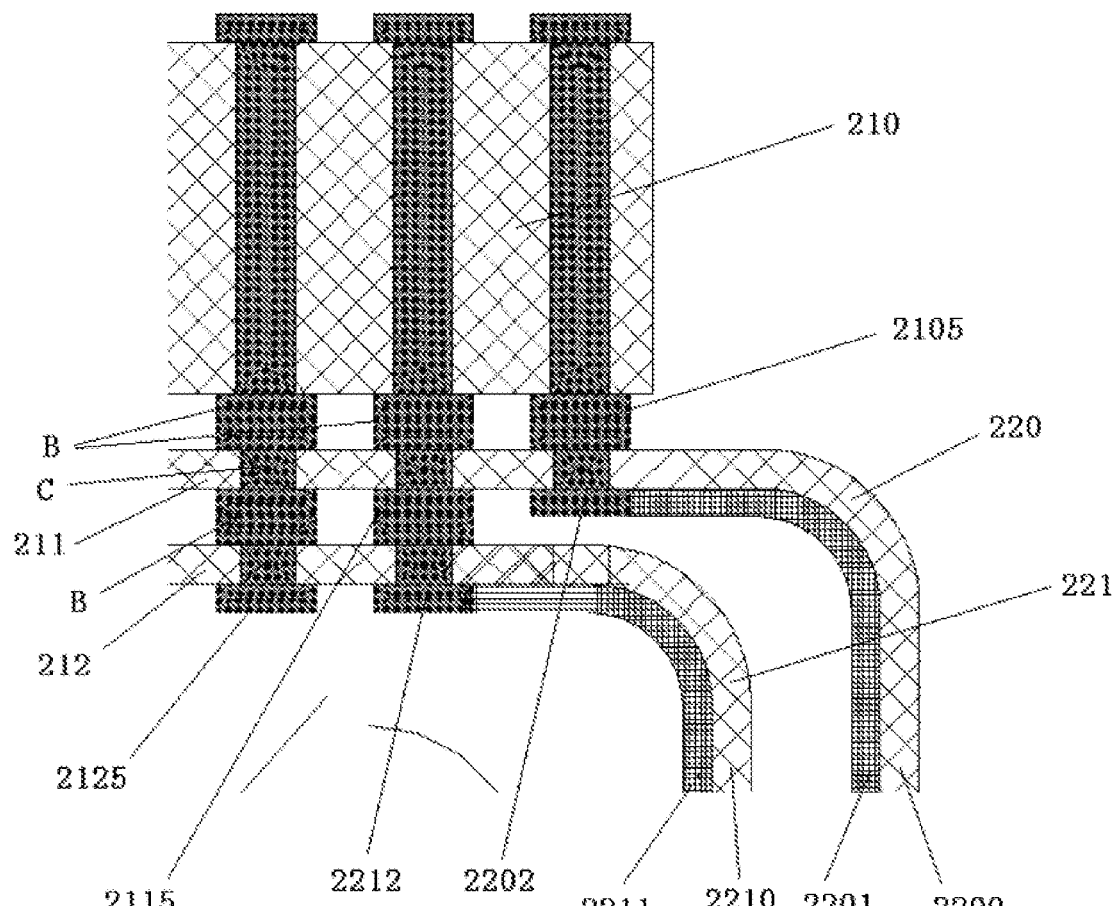
FIG. 12 is an enlarged view of the region marked A in FIG. 11.

For example, another embodiment of the connection component for array elements 21 and signal transmission line component 22 in an ultrasonic probe is shown in FIG. 11 and FIG. 12. In one embodiment, the signal transmission line component 22 may have a plurality of groups of signal transmission lines, and each group of signal transmission lines is provided with a substrate layer and a wire formed on the substrate layer. For example, the first-group signal transmission line 220 may have a first-group substrate layer 2200 and a first-group wire 2201 formed on the first-group substrate layer 2200; the second-group signal transmission line 221 may have a second-group substrate layer 2210 and a second-group wire 2211 formed on the second-group substrate layer 2210. In a similar manner, other groups of signal transmission lines may have respective substrate layers and respective wires, e.g., the third-group signal transmission line may include a third-group substrate layer and a third-group wire may be formed on the third-group substrate layer (not shown in FIG. 11 and FIG. 12), and the fourth-group signal transmission line may include a fourth-group substrate layer and a fourth-group wire formed on the fourth-group substrate layer (not shown in FIG. 11 and FIG. 12), and so forth.

In one embodiment, the first-layer body 210 may be identical to or similar to the first-layer body 210 mentioned in foregoing embodiments. It is different from the foregoing embodiments in that at least one layer of the body below the first-layer body 210 may be molded integrally with a substrate layer of a signal transmission line of its adjacent and upper layer of body, or one layer of the body below the first-layer body 210 may be an extension part of the substrate layer of the signal transmission line of its adjacent and upper layer body. For example, as shown in FIG. 11 and FIG. 12, the second-layer body 211 may be molded integrally with the first-group substrate layer 2200 of the first-group signal transmission line 220, and the signal transmission line is connected with the first-layer conductive element 2105 located on the first-layer wiring connection region 2100 of the first-layer body 210. Alternatively, the second-layer body 211 may be an extension part of the first-group substrate layer 2200. The third-layer body 212 may be molded integrally with the second-group substrate layer 2210 of the second-group signal transmission line 221, and the second-group signal transmission line 221 is connected with the second-layer conductive element 2115 located on the second-layer wiring connection region 2110 of the second-layer body 211; alternatively, the third-layer body 212 may be extension part of the second-group substrate layer 2210. Similarly, if there are more bodies below the third-layer body 212, each of them may be formed in a similar manner. For example, the fourth-layer body may be molded integrally with the third-group substrate layer of the third-group signal transmission line, and the third-group signal transmission line is connected with the third-layer conductive element located on the third-layer wiring connection region of the third-layer body. Alternatively, the fourth-layer body may be extension of part of the third-group substrate layer, and so forth.

It is noted that, in FIG. 11 and FIG. 12, the structure of each body below the third-layer body 212 may be similar to that of the second-layer body 211 and the third-layer body 212, but the quantity of conductive elements passing through each body may gradually decrease from upper body to lower body, wherein the quantity of conductive elements in one layer of body may include those belonging to said body itself and those passing through said body but belonging to the other body that is below said body. Similarly, the structure of the signal transmission line connected to the conductive element of each body below the third-layer body 212 may be similar to that of the first-group signal transmission line 220 and the second-group signal transmission line 221. Therefore, each body and corresponding signal transmission line below the third-layer body 212 is not described in detail and is schematically illustrated with a thin solid line in FIG. 11 and FIG. 12 instead.

An end of the first-group wire 2201 of the first-group signal transmission line 220 is provided with a first-group wire contact point 2202, and an end of the second-group wire 2211 of the second-group signal transmission line 221 is provided with a second-group wire contact point 2212. The first-group wire 2201 may be connected to the first-layer conductive element 2105 of the first-layer body 210 through a first-group wire contact point 2202, which may pass through a first-group substrate layer 2200. The second-group wire 2211 may be connected to the second-layer conductive element 2115 of the second-layer body 211 through a second-group wire contact point 2212, which may pass through a second-group substrate layer 2210. Similarly, other signal transmission lines (if there are any) may also have a similar structure and connect in a similar manner. For example, the third-group wire may be connected to the third-layer conductive element of the third-layer body through a third-group wire contact point (not shown in FIG. 11 and FIG. 12) and so forth.

In one embodiment as shown in FIG. 11 and FIG. 12, the wire and wire contact point of each group of signal transmission line may be arranged below the corresponding substrate layer. However, it would be understood that, in other embodiments, the wire and wire contact point of each group of signal transmission lines may be arranged above the corresponding substrate layer; in this option, when the wire is connected to the corresponding conductive element of the corresponding body through the corresponding wire contact point, there may be no need to pass through the corresponding substrate layer.

In one embodiment, the ends of conductive elements of each body, such as the ends of first-layer conductive element 2105 and the second-layer conductive element 2115, etc., for connecting with a corresponding signal transmission line, may be made in any form suitable for electrical connection, for example, in the form of pads (shown in FIG. 7 or FIG. 12).

Other features in one embodiment can be identical or similar to those in foregoing embodiments, which will not be repeated herein.

In one embodiment, each layer of conductive elements passing bodies, such as the second-layer conductive element 2115, the third-layer conductive element 2125, the fourth-layer conductive element 2155 and the fifth-layer conductive element 2165 in FIG. 7, or the second-layer conductive element 2115 and the third-layer conductive element 2125, and so on, may have contact points B to facilitate manufacture, which are located between passed bodies, if the bodies are separated and then connected together in the manner described in above embodiments. The contact points B are identical to or similar to the wire contact point of the signal transmission line, such the first-group wire contact point 2202 or the second-group wire contact point 2212 as shown in FIG. 12. Accordingly, in manufacturing, the contact points may first be formed on both sides of each layer of body and each pair of contact points of one layer may be connected to each other by a conductive material C passing through the corresponding body. Then, the contact points on each body may be connected accordingly to when layers of body are connected to each other. Finally, the contact points B connected between each layer of body and the conductive material C may constitute the conductive element of each layer of body mentioned above, when layers of body are connected to each other. In other words, in one embodiment, the "conductive element" in each layer of body may be constituted by several parts connected to each other. Alternatively, as previously described, the "conductive element" in each layer of body may an integrally molded component, such as conductive element 2115, 2125, 2155, 2165, etc., shown in FIG. 9.

In one embodiment, the layer quantity of bodies in the connection component for array elements 21 may be flexibly configured according to an actual design, as long as the connection component for array elements 21 has at least two layers of bodies, which may be flexibly configured according to an actual design and/or quantity and/or dimension of the probe, the array element assembly 20, the connection component for array elements and the signal transmission line, as long as it has at least two layers of bodies.

In one embodiment, the quantity and arrangement of the conductive elements in the connection component for array elements 21 of each layer of body may be configured flexibly based on an actual design, which will not be limited to a particular quantity and arrangement in the present disclosure.

In the foregoing embodiments, when referring to a "group" of components, such as the first-group signal transmission line, the second-group signal transmission line, the first-group substrate layer, the second-group substrate layer, etc., the "group" of components may be only one component or may contain a plurality of components.

Figure 13:
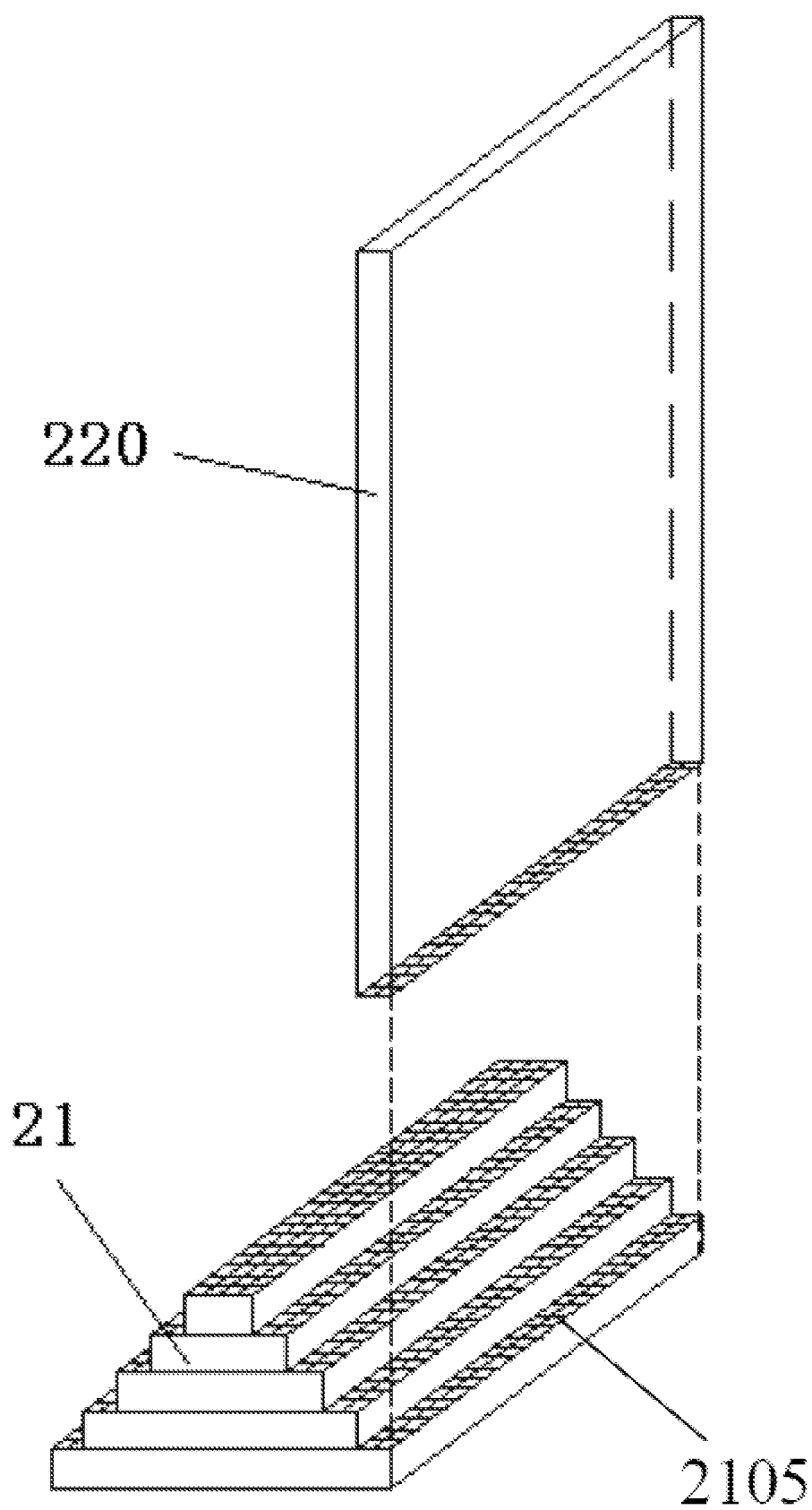
FIG. 13 is a diagram of connection between a signal transmission line and a connection component for array elements in another embodiment.

In the foregoing embodiments, the first-group signal transmission line 220 may be connected with the first-layer conductive element 2105 of the wiring connection region of each layer of body in any suitable manner. For example, as shown in FIG. 2 or FIG. 11, the extension direction of the first-group signal transmission line 220 may be perpendicular to that of the first-layer conductive element 2105. Alternatively, as shown in FIG. 13, the extension direction of the first-group signal transmission line 220 may be parallel to or coincide with that of the first-layer conductive element 2105.

Figure 14:
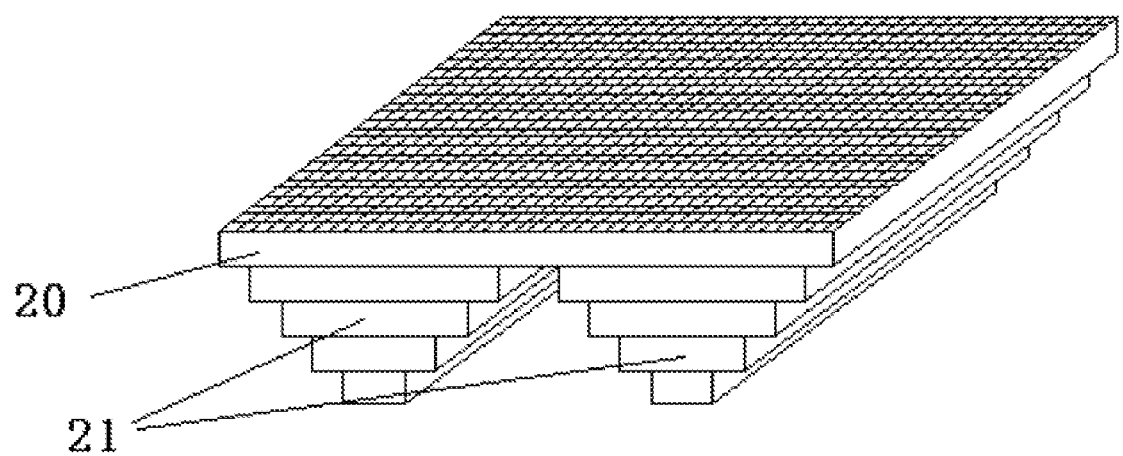
FIG. 14 is a perspective view of an array element assembly and a connection component for array elements in another embodiment.
Figure 15:
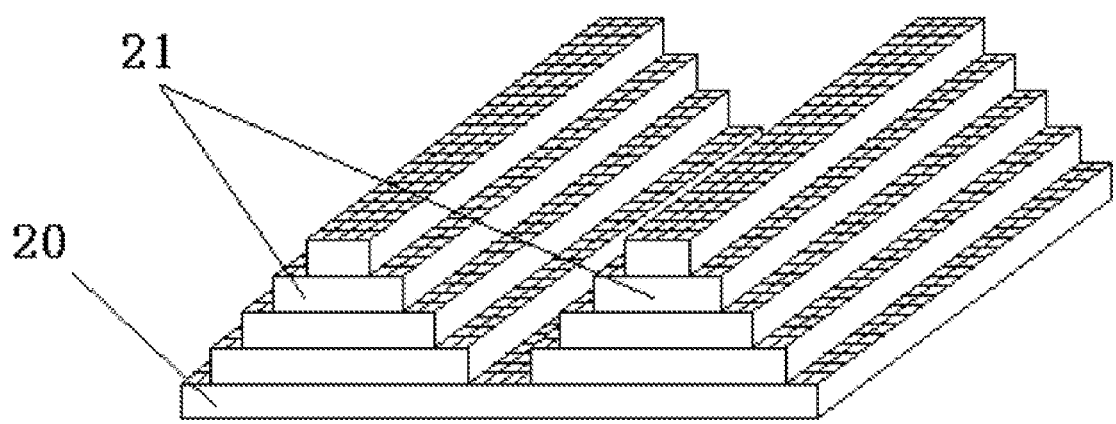
FIG. 15 is another perspective view of an array element assembly and a connection component for array elements shown in FIG. 14.

In still another embodiment, a transducer 2 of the ultrasonic probe may include more than one connection component for array elements 21; instead, it may have a plurality of connection components for array elements 21. That is, an array element assembly 20 may be connected to the more than one connection component for array elements 21. In one embodiment as shown in FIG. 14 and FIG. 15, the array element assembly 20 is connected to two connection components for array elements 21. In one embodiment, the array element assembly 20 may be connected to at least one connection component for array elements 21, that is, the ultrasonic probe may have at least one connection component for array elements.

Herein, when referring to an "above/upper" or "below/lower" position, it means the ultrasonic probe is placed vertically and the ultrasonic head is upward.

Accordingly, an ultrasonic imaging system is provided in still another embodiment of the present disclosure, which includes a host and any one of the ultrasonic probes mentioned above. The ultrasonic probe may be connected to the host which may receive ultrasonic echoes and make the ultrasonic probe emit ultrasonic waves, so as to achieve ultrasonic scanning and imaging. In one embodiment, the host may be a conventional host employed in a field of ultrasonic imaging.

In one embodiment, the connection component for array elements may be in a stepped shape. The signal transmission line may be connected to an array element assembly through the stepped connection component, so there might be sufficient space for interconnection between the array element assembly and the signal transmission line, such as an FPC, PCB, cable, etc.

In one embodiment, since the stepped connection component for array elements may be an integral component, there may be a reduction in the alignment requirement and assembly difficulty when it is interconnected with array elements in the array element assembly. At the same time, signal transmission lines, such as an FPC, PCB, cable, etc., may engender a multi-layer structure when they are connected with the stepped connection component for array elements, because the latter has a multi-layered structure. Thus there might be sufficient space for the signal transmission lines. Moreover, the quantity of the body of the stepped connection component for array elements might be reasonably selected in accordance with the quantity of the array elements in the array element assembly, the processing difficulty of the stepped connection component for array elements, and the quantity of corresponding array element controlling components. As a result, the signal transmission lines might be arranged easily and flexibly, and the interference problem and difficulty of wiring arrangement caused by complicated and compact wiring might be reduced, and the interconnection between the array element assembly and corresponding array element controlling component via the signal transmission line might be improved with less cost.

The foregoing embodiments with detailed descriptions represent several implementations of the present disclosure, but they should not be construed as limiting the scope of the present disclosure. It should be noted that, for those skilled in the art, a number of modifications and improvements can also be made without departing from the idea of the present disclosure, which is within the claimed scope of the present disclosure. Therefore, the claimed scope of the present disclosure should be subject to the appended claims.

We claim that:

1. A connection component in an ultrasonic probe, comprising:
    a first-layer body comprising a first upper surface and a first-layer wiring connection region arranged on a first lower surface of the first-layer body;
    a second-layer body connected to the first-layer body and comprising a second-layer wiring connection region arranged on a second lower surface of the second-layer body;
    a first-layer conductive element arranged on the first-layer wiring connection region and extended to the first upper surface of the first-layer body by penetrating through the first-layer body; and a second-layer conductive element arranged on the second-layer wiring connection region and extended to the first upper surface of the first-layer body by penetrating through the second-layer body and the first-layer body.

2. The connection component of claim 1, further comprising:

a third-layer body connected to the second-layer body and comprising a third-layer wiring connection region arranged on a third lower surface of the third-layer body; and a third-layer conductive element arranged on the third-layer wiring connection region and extended to the first upper surface of the first-layer body by penetrating through the third-layer body, the second-layer body and the first-layer body.

3. An ultrasonic probe, comprising a transducer, wherein the transducer comprises:

an array element assembly comprising a plurality of array elements; and a connection component comprising:

a first-layer body comprising a first upper surface and a first-layer wiring connection region arranged on a first lower surface of the first-layer body, wherein a plurality of conductive contacts are arranged on the first upper surface and each conductive contact is connected to one of the array elements respectively;

a second-layer body connected to the first-layer body and comprising a second-layer wiring connection region arranged on a second lower surface of the second-layer body;

a plurality of first-layer conductive elements arranged on the first-layer wiring connection region and extended to the first upper surface of the first-layer body by penetrating through the first-layer body, wherein each first-layer conductive element is connected to one of the conductive contacts; and a plurality of second-layer conductive elements arranged on the second-layer wiring connection region and extended to the first upper surface of the first-layer body by penetrating through the second-layer body and the first-layer body, wherein each second-layer conductive element is connected to one of the conductive contacts.

4. The ultrasonic probe of claim 3, wherein the transducer further comprises:

a first-group signal transmission line connected to the plurality of first-layer conductive elements; and a second-group signal transmission line connected to the plurality of second-layer conductive elements.

5. The ultrasonic probe of claim 4, wherein:

the first-group signal transmission line is provided with a first-group substrate layer and a first-group wire formed on the first-group substrate layer;

the second-group signal transmission line is provided with a second-group substrate layer and a second-group wire formed on the second-group substrate layer;

the second-layer body is an extension part of the first-group substrate layer;

the first-group wire is connected to the first-layer conductive element; and the second-group wire is connected to the second-layer conductive element.

6. The ultrasonic probe of claim 3, wherein:

the connection component further comprises:

a third-layer body connected to the second-layer body and comprising a third-layer wiring connection region arranged on a third lower surface of the third-layer body; and a plurality of third-layer conductive elements arranged on the third-layer wiring connection region and extended to the first upper surface of the first-layer body by penetrating through the third-layer body, the second-layer body and the first-layer body, wherein each third-layer conductive element is connected to one of the conductive contacts.

7. The ultrasonic probe of claim 6, wherein the ultrasonic transducer further comprises:

a first-group signal transmission line connected to the plurality of first-layer conductive elements;

a second-group signal transmission line connected to the plurality of second-layer conductive elements; and a third-group signal transmission line connected to the plurality of third-layer conductive elements.

8. The ultrasonic probe of claim 7, wherein:

the first-group signal transmission line is provided with a first-group substrate layer and a first-group wire formed on the first-group substrate layer;

the second-group signal transmission line is provided with a second-group substrate layer and a second-group wire formed on the second-group substrate layer;

the third-group signal transmission line is provided with a third-group substrate layer and a third-group wire formed on the third-group substrate layer;

the second-layer body is an extension part of the first-group substrate layer;

the third-layer body is an extension part of the second-group substrate layer;

the first-group wire is connected to the first-layer conductive element;

the second-group wire is connected to the second-layer conductive element; and the third-group wire is connected to the third-layer conductive element.

9. The ultrasonic probe of claim 3, wherein the first upper surface is provided with a plurality of conductive contacts and each conductive contract is electrically connected to one of the array elements.

10. The ultrasonic probe of claim 3, wherein each array element comprises a transducer element and a backing block connected with the transducer element.

11. The ultrasonic probe of claim 10, wherein the first-layer body, the second-layer body and the backing block are made of same material.

12. An ultrasonic imaging system, comprising an ultrasonic probe which comprises a transducer, wherein the transducer comprises:

an array element assembly comprising a plurality of array elements; and a connection component comprising:

a first-layer body comprising a first upper surface and a first-layer wiring connection region arranged on a first lower surface of the first-layer body, wherein a plurality of conductive contacts are arranged on the first upper surface and each conductive contact is connected to one of the array elements respectively;

a second-layer body connected to the first-layer body and comprising a second-layer wiring connection region arranged on a second lower surface of the second-layer body;

a plurality of first-layer conductive elements arranged on the first-layer wiring connection region and extended to the first upper surface of the first-layer body by penetrating through the first-layer body, wherein each first-layer conductive element is connected to one of the conductive contacts; and a plurality of second-layer conductive elements arranged on the second-layer wiring connection region and extended to the first upper surface of the first-layer body by penetrating through the second-layer body and the first-layer body, wherein each second-layer conductive element is connected to one of the conductive contacts.

* * * * *